United States Patent
Kern et al.

(10) Patent No.: US 10,307,290 B2
(45) Date of Patent: Jun. 4, 2019

(54) VITREOUS CUTTER WITH INTEGRATED ILLUMINATION SYSTEM

(71) Applicant: Novartis AG, Basel (CH)

(72) Inventors: Thomas Kern, Lucerne (CH); Alireza Mirsepassi, Irvine, CA (US); Michael J. Papac, North Tustin, CA (US); Ronald T. Smith, Irvine, CA (US); Barry L. Wheatley, Oceanside, CA (US)

(73) Assignee: Novartis AG, Basel (CH)

( * ) Notice: Subject to any disclaimer, the term of this patent is extended or adjusted under 35 U.S.C. 154(b) by 258 days.

(21) Appl. No.: 15/202,896

(22) Filed: Jul. 6, 2016

(65) Prior Publication Data
US 2017/0014267 A1    Jan. 19, 2017

Related U.S. Application Data

(60) Provisional application No. 62/191,765, filed on Jul. 13, 2015.

(51) Int. Cl.
*A61F 9/007* (2006.01)
*A61B 90/30* (2016.01)
*A61B 17/00* (2006.01)

(52) U.S. Cl.
CPC .......... *A61F 9/00736* (2013.01); *A61B 90/30* (2016.02); *A61B 2017/00973* (2013.01);
(Continued)

(58) Field of Classification Search
CPC ............... A61B 90/30; A61B 2090/306; A61F 9/00736; A61F 9/00745; A61F 9/00763
(Continued)

(56) References Cited

U.S. PATENT DOCUMENTS 3,449,037 A * 6/1969 Koester ............... G02B 6/06
346/33 R
3,990,453 A 11/1976 Douvas et al.
(Continued)

FOREIGN PATENT DOCUMENTS

AU      741736      3/1999
EP      0260856 A2  3/1988
(Continued)

OTHER PUBLICATIONS

Fisher et al., Inexpensive Illuminated Vitrectomy Cutter, The Journal of Retinal and Vitreous Diseases, Dec. 2003, vol. 23, Issue 6, p. 891.
(Continued)

*Primary Examiner* — Kathleen S Holwerda (57) ABSTRACT

An illuminated microsurgical instrument is provided herein that includes a microsurgical instrument having a tubular member arranged to treat patient tissue at a surgical site, the tubular member having a distal tip, an inner surface, and an outer surface. The inner surface defines a lumen. The outer surface has a notch formed therein. The illuminated microsurgical instrument further includes an optical fiber arranged to deliver light to the surgical site. The optical fiber includes a proximal end arranged to receive a light beam from a light source and also includes a curved distal end arranged to emit light adjacent to the distal tip. A portion of the curved distal end is positioned within the notch and curves away from the tubular member.

21 Claims, 9 Drawing Sheets

(52) U.S. Cl.
CPC ... *A61B 2090/306* (2016.02); *A61B 2217/005* (2013.01); *A61B 2217/007* (2013.01)

(58) Field of Classification Search
USPC ........................................................ 600/182
See application file for complete search history.

(56) References Cited

U.S. PATENT DOCUMENTS

| | | | |
|---|---|---|---|
| 4,011,869 A | | 3/1977 | Seiler, Jr. |
| 4,168,707 A | | 9/1979 | Douvas et al. |
| 4,200,106 A | | 4/1980 | Douvas et al. |
| 4,607,622 A | | 8/1986 | Fritch et al. |
| 4,826,280 A | * | 5/1989 | Hiramoto ........... A61B 1/00073 385/116 |
| 4,872,837 A | | 10/1989 | Issalene et al. |
| 4,909,249 A | | 3/1990 | Akkas et al. |
| 5,047,008 A | * | 9/1991 | de Juan, Jr. ......... A61F 9/00763 600/564 |
| 5,201,730 A | | 4/1993 | Easley et al. |
| 5,275,593 A | | 1/1994 | Easley et al. |
| 5,280,788 A | | 1/1994 | Janes et al. |
| 5,281,214 A | | 1/1994 | Wilkins et al. |
| 5,357,168 A | | 10/1994 | See |
| 5,402,508 A | | 3/1995 | O'Rourke et al. |
| 5,425,730 A | | 6/1995 | Luloh |
| 5,554,155 A | | 9/1996 | Awh et al. |
| 5,588,952 A | | 12/1996 | Dandolu |
| 5,591,160 A | | 1/1997 | Reynard |
| 5,651,783 A | | 7/1997 | Reynard |
| 5,667,472 A | | 9/1997 | Finn et al. |
| 5,681,264 A | | 10/1997 | Ryan, Jr. |
| 5,716,363 A | | 2/1998 | Josephberg |
| 5,733,297 A | | 3/1998 | Wang |
| 5,785,645 A | | 7/1998 | Scheller |
| 5,916,149 A | | 6/1999 | Ryan, Jr. |
| 5,931,670 A | | 8/1999 | Davis |
| 5,964,747 A | | 10/1999 | Eaton et al. |
| 6,120,518 A | * | 9/2000 | Mark ................... A61B 90/36 606/170 |
| 6,193,650 B1 | | 2/2001 | Ryan, Jr. |
| 6,254,530 B1 | | 7/2001 | Ryan, Jr. |
| 6,322,557 B1 | | 11/2001 | Nikolaevich et al. |
| 6,366,726 B1 | | 4/2002 | Wach et al. |
| 6,939,341 B2 | | 9/2005 | Vijfvinkel |
| 7,783,346 B2 | | 8/2010 | Smith et al. |
| 7,972,326 B2 | | 7/2011 | Scheller |
| 8,038,692 B2 | | 10/2011 | Valencia et al. |
| 8,075,553 B2 | | 12/2011 | Scheller et al. |
| 8,900,139 B2 | | 12/2014 | Yadlowsky et al. |
| 8,968,347 B2 | | 3/2015 | McCollam |
| 8,979,867 B2 | | 3/2015 | Peyman |
| 9,055,885 B2 | | 6/2015 | Horvath et al. |
| 9,066,678 B2 | | 6/2015 | Auld et al. |
| 9,089,364 B2 | | 7/2015 | Bhadri et al. |
| 9,364,982 B2 | | 6/2016 | Schaller |
| 9,402,643 B2 | | 8/2016 | Auld et al. |
| 9,510,848 B2 | | 12/2016 | Auld et al. |
| 9,561,085 B2 | | 2/2017 | Yadlowsky et al. |
| 9,839,749 B2 | | 12/2017 | Johnson et al. |
| 9,956,053 B2 | | 5/2018 | Diao et al. |
| 10,016,248 B2 | | 7/2018 | Mirsepassi et al. |
| 10,039,669 B2 | | 8/2018 | Heeren |
| 2005/0251119 A1 | * | 11/2005 | Eaton .................. G02B 6/0008 606/15 |
| 2007/0100327 A1 | | 5/2007 | Smith |
| 2009/0161384 A1 | | 6/2009 | Smith |
| 2009/0163897 A1 | | 6/2009 | Skinner |
| 2009/0182313 A1 | | 7/2009 | Auld |
| 2009/0221991 A1 | | 9/2009 | Lieponis |
| 2011/0125139 A1 | | 5/2011 | Auld |
| 2011/0282160 A1 | | 11/2011 | Bhadri et al. |
| 2012/0147329 A1 | | 6/2012 | Papac et al. |
| 2012/0203075 A1 | | 8/2012 | Horvath et al. |
| 2012/0283523 A1 | * | 11/2012 | Yadlowsky ......... A61F 9/00763 600/249 |
| 2012/0330101 A1 | | 12/2012 | Brennan et al. |
| 2013/0079598 A1 | * | 3/2013 | Auld .................... A61B 3/0008 600/249 |
| 2014/0121469 A1 | | 5/2014 | Meckel et al. |
| 2014/0357957 A1 | | 12/2014 | Bhadri et al. |
| 2015/0219819 A1 | * | 8/2015 | Sun ........................ G02B 6/32 362/553 |
| 2016/0113722 A1 | | 4/2016 | Heeren |
| 2016/0120699 A1 | | 5/2016 | Farley |
| 2017/0014023 A1 | | 1/2017 | Kern |
| 2017/0119491 A1 | | 5/2017 | Mirsepassi et al. |
| 2017/0165114 A1 | | 6/2017 | Hallen et al. |
| 2018/0055596 A1 | | 3/2018 | Johnson |
| 2018/0132963 A1 | | 5/2018 | Diao et al. |
| 2018/0133057 A1 | | 5/2018 | Diao et al. |
| 2018/0168768 A1 | | 6/2018 | Mirsepassi et al. |
| 2018/0168861 A1 | | 6/2018 | Mirsepassi et al. |

FOREIGN PATENT DOCUMENTS

| | | |
|---|---|---|
| EP | 0651981 A1 | 5/1995 |
| GB | 1349881 | 4/1974 |
| JP | S52-10346 A3 | 4/1968 |
| JP | 05-220170 A7 | 8/1993 |
| JP | 2002245821 A | 8/2002 |
| JP | 2007260192 A | 10/2007 |
| WO | 9948557 A1 | 9/1999 |
| WO | 2003045290 A1 | 6/2003 |
| WO | 2004002337 A1 | 1/2004 |
| WO | 2009091462 A1 | 7/2009 |
| WO | 2014183123 A1 | 11/2014 |
| WO | 2016064580 A1 | 4/2016 |

OTHER PUBLICATIONS

Chalam, et al., Illuminated Curved Vitrectomy Probe for Vitreoretinal Surgery, Ophthalmic Surgery, Lasers and Imaging, Nov./Dec. 2007—vol. 38 Â—Issue 6: 525-526.

Alcon Updated Vitreoretinol Product Catalog 2009, pp. 27-28.

Calhoun, et al., The Roto-Extractor in Pediatric Ophthalmology, Tr. Am. Ophth. Soc., vol. LXXIII, 1975, 14 pages.

DORC: Focus on New Instruments 2009/2010 catalog; Version 2009.1; 2009 D.O.R.C. International b.v; Dutch Ophthalmic USA Inc.

Douvas, Microsurgical Roto-Extractor Instrument for Vitrectomy, New Research on the Aetiology and Surgery of Retinal Detachment Mod. Probl. Ophthal., vol. 15, pp. 253-260 (Karger, Basel 1975), Port Huron, Michigan, USA.

Meadow, MD, Facs; Norman B.; Vitreous history in the making; Ophthalmology Times, Jul. 15, 2013.

Museum of Vision: Collection Objects; The Foundation of the American Academy of Ophthalmology; http://www.museumofvision.org/collection/artifacts?accession=2004.004.00001, accessed Feb. 26, 2015.

\* cited by examiner

VITREOUS CUTTER WITH INTEGRATED ILLUMINATION SYSTEM

TECHNICAL FIELD

The present disclosure is directed to methods and systems for medical procedures, and more particularly, to methods and systems involving a need for illumination within a body cavity.

BACKGROUND

Vitreo-retinal procedures are commonly performed to treat many serious conditions of the posterior segment of the eye. For example, vitreo-retinal procedures may treat conditions such as age-related macular degeneration (AMD), diabetic retinopathy and diabetic vitreous hemorrhage, macular hole, retinal detachment, epiretinal membrane, cytomegalovirus (CMV) retinitis, and many other ophthalmic conditions.

A surgeon performs vitreo-retinal procedures with a microscope and special lenses designed to provide a clear image of the posterior segment. Several tiny incisions just a millimeter or so in diameter are made on the sclera at the pars plana. The surgeon inserts microsurgical instruments through the incisions, such as a fiber optic light source to illuminate inside the eye, an infusion line to maintain the eye's shape during surgery, and instruments to cut and remove the vitreous body. A separate incision may be provided for each microsurgical instrument when using multiple instruments simultaneously.

During such surgical procedures, proper illumination of the inside of the eye is important. Typically, an optical fiber is inserted into one of the incisions in the eye to provide the illumination. A light source, such as a halogen tungsten lamp or high pressure arc lamp (metal-halides, Xe), may be used to produce the light carried by the optical fiber into the eye. The light passes through several optical elements (typically lenses, mirrors, and attenuators) and is transmitted to the optical fiber that carries the light into the eye.

The incisions are typically only made large enough to accommodate the size of the microsurgical instrument being inserted into the interior of the eye. Efforts to minimize the incision size generally involve reducing the size of the microsurgical instrument. However, a reduction in size can result in a reduction in strength or rigidity. Depending on the size of the microsurgical instrument employed, the incision may be small enough to render a resulting wound substantially self-healing, thereby eliminating the need to employ additional procedures to close the incision, such as sutures. Also, reducing the number of incisions may be accomplished by integrating various microsurgical instruments. For example, the optical fiber may be incorporated into the working end of a microsurgical instrument. This may eliminate the need for a separate illumination incision, and offers the advantage of directing the light beam, together with the microsurgical instrument, onto the target site through a common opening in the sclera. Unfortunately, at least some prior attempts at integrating illuminating optical fibers with microsurgical instruments have resulted in a decrease in illuminating efficiency or in other visualization problems that otherwise adversely effected the distribution of light emitted from the optical fibers.

SUMMARY

The present disclosure is directed to exemplary illuminated microsurgical instruments. The instruments may include a microsurgical instrument and an optical fiber for delivering light to a surgical site. An exemplary instrument may include a microsurgical instrument having a tubular member arranged to treat patient tissue at the surgical site, such as within a body cavity. The tubular member may have a distal tip and an outer surface. The outer surface may have a notch formed therein. The illuminated microsurgical instrument may further include an optical fiber arranged to deliver light to the surgical site. The optical fiber may include a proximal end arranged to receive a light beam from a light source and may also include a curved distal end arranged to emit light adjacent to the distal tip. A portion of the curved distal end may be positioned within the notch and may curve away from the tubular member.

Exemplary surgical systems are provided herein. An exemplary surgical system may include a light source coupleable to an optical fiber to provide illumination at a distal end of the optical fiber and may further include a vitrectomy subsystem having a vitrectomy cutter. The vitrectomy cutter may include a tubular member with a distal tip and a lumen extending therein. The lumen may be defined by an inner surface of a wall of the tubular member. The distal tip may include a port extending through the wall of the tubular member. The optical fiber may be arranged to deliver light to a surgical site. As such, the optical fiber may include a proximal end for receiving a light beam from the light source and a distal end arranged to emit light adjacent to the port. A portion of the distal end may be positioned within a notch that extends from an outer surface of the tubular member into the wall. A tip of the distal end may be directed away from the tubular member in order to minimize glare produced by the light reflecting off a portion of the tubular member.

Exemplary vitrectomy cutters are provided herein. An exemplary vitrectomy cutter may include a tubular member arranged to remove vitreous from with an eye of a patient and an optical fiber arranged to deliver light into the eye to provide illumination for a surgical procedure performed therein. The tubular member may have a distal tip and a lumen extending therein. The lumen may be defined by an inner surface of a wall of the tubular member. The distal tip of the tubular member may include a port extending through the wall of the tubular member to receive vitreous into the lumen during a vitrectomy procedure. To illuminate the cavity of the eye, the optical fiber may include a proximal end to receive a light beam from a light source and may also include a distal end arranged to emit light adjacent to the port. A portion of the distal end may be positioned within a notch formed in an outer surface of the tubular member. A portion of the distal end may be directed away from the tubular member to better illuminate an area of interest to a surgeon performing the procedure.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate embodiments of the devices and methods disclosed herein and together with the description, serve to explain the principles of the present disclosure.

The accompanying drawings may be better understood by reference to the following detailed description.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure is directed to methods and systems for providing illumination within a body cavity during an operation performed therein without requiring a separate incision to be made for the illumination source. In some examples, the illumination is provided through an optical fiber extending along a length of another surgical tool within the body cavity. For example, a vitrectomy procedure may be performed to remove vitreous from the eye of a patient using a vitrectomy cutter and introduced into the eye with the vitrectomy cutter. Rather than form two incisions in the eye of the patient, the optical fiber may be positioned along a portion of the vitrectomy cutter. The optical fiber may have a distal tip through which light is introduced or emitted into the posterior chamber of the eye. The removal of the vitreous may be of particular importance, because residual vitreous can cause post-operative retinal tearing, retinal detachment, etc.

In order to visualize the vitreous, which is generally clear, some implementations may concentrate the lighting in the near field and diffuse lighting in the far field in order to prevent hot spots from forming on the retina. The vitreous may be visualized due to light scattering off the fibers contained within it. The lighting may be positioned proximate the cutting portion of the vitrectomy cutter in order to better visualize the vitreous being cut. Depending on the implementation, the optical fiber may include a curved distal end that is angled away from a main tube of the vitrectomy cutter in order to minimize the production of glare off the distal tip of the vitrectomy cutter. Thus, embodiments of the present disclosure provide for improved illumination for inner-cavity procedures, such as vitrectomy procedures, while minimizing the number of incisions required to be made to permit entry to the cavity. The illumination provided by embodiments of the present disclosure may result in high irradiance at the surgical site, e.g. at the port of the vitrectomy cutter. This may provide for a high signal to noise ratio or contrast to facilitate visualization of the fibers in the vitreous.

Figure 1:
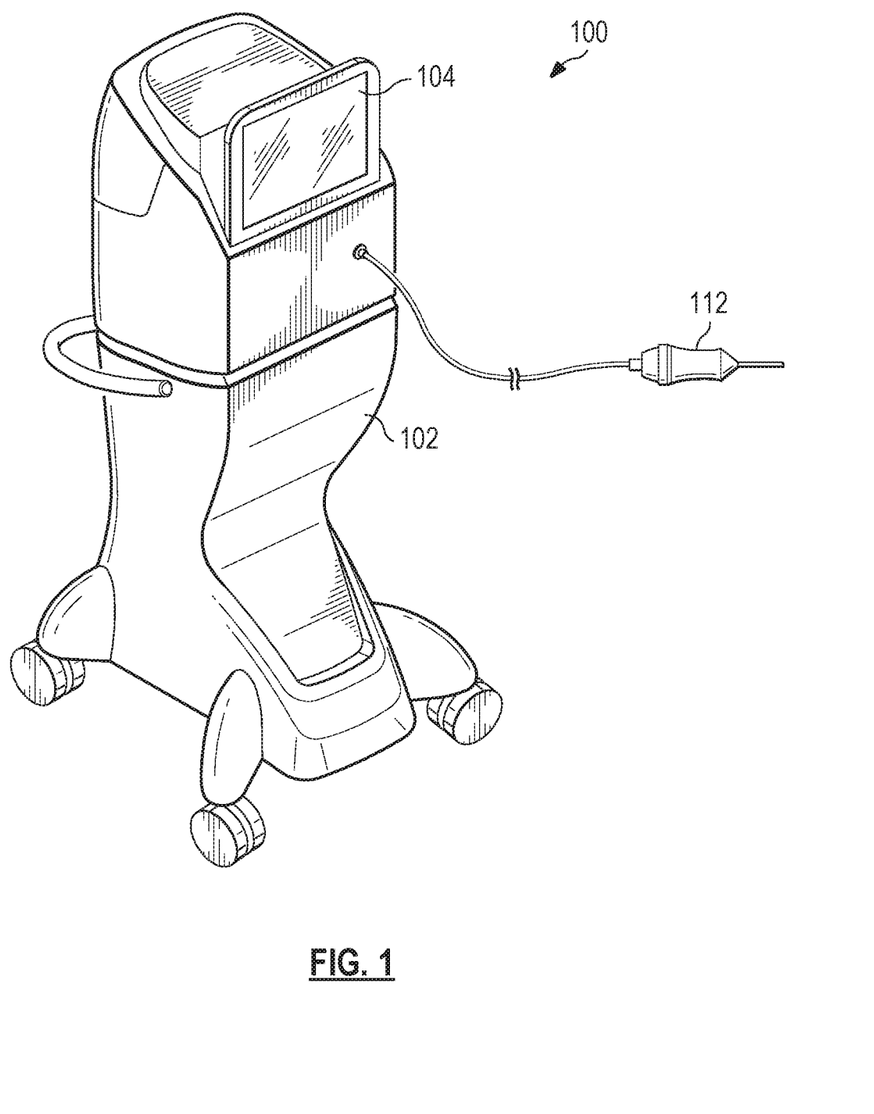
FIG. 1 illustrates a perspective view of an exemplary surgical system, according to an embodiment consistent with the principles of the present disclosure.

FIG. 1 illustrates a vitrectomy surgical system, generally designated 100, according to an exemplary embodiment. The surgical system 100 includes a base housing or console 102 and an associated display screen 104 showing data relating to system operation and performance during a vitrectomy surgical procedure. In an embodiment, the console 102 may be mobile, for example including wheels to facilitate movement as necessary. In an alternative embodiment, the console 102 may not include wheels. The console 102 may be referred to as a "base housing" and include a plurality of subsystems that cooperate to enable a surgeon to perform a variety of surgical procedures, such as ophthalmic surgical procedures. An illuminated vitrectomy probe 112, referred to as a handpiece, may attach to the console 102 and may form a part of the surgical system 100. The illuminated vitrectomy probe 112 may form part of a vitrectomy subsystem described herein.

Figure 2:
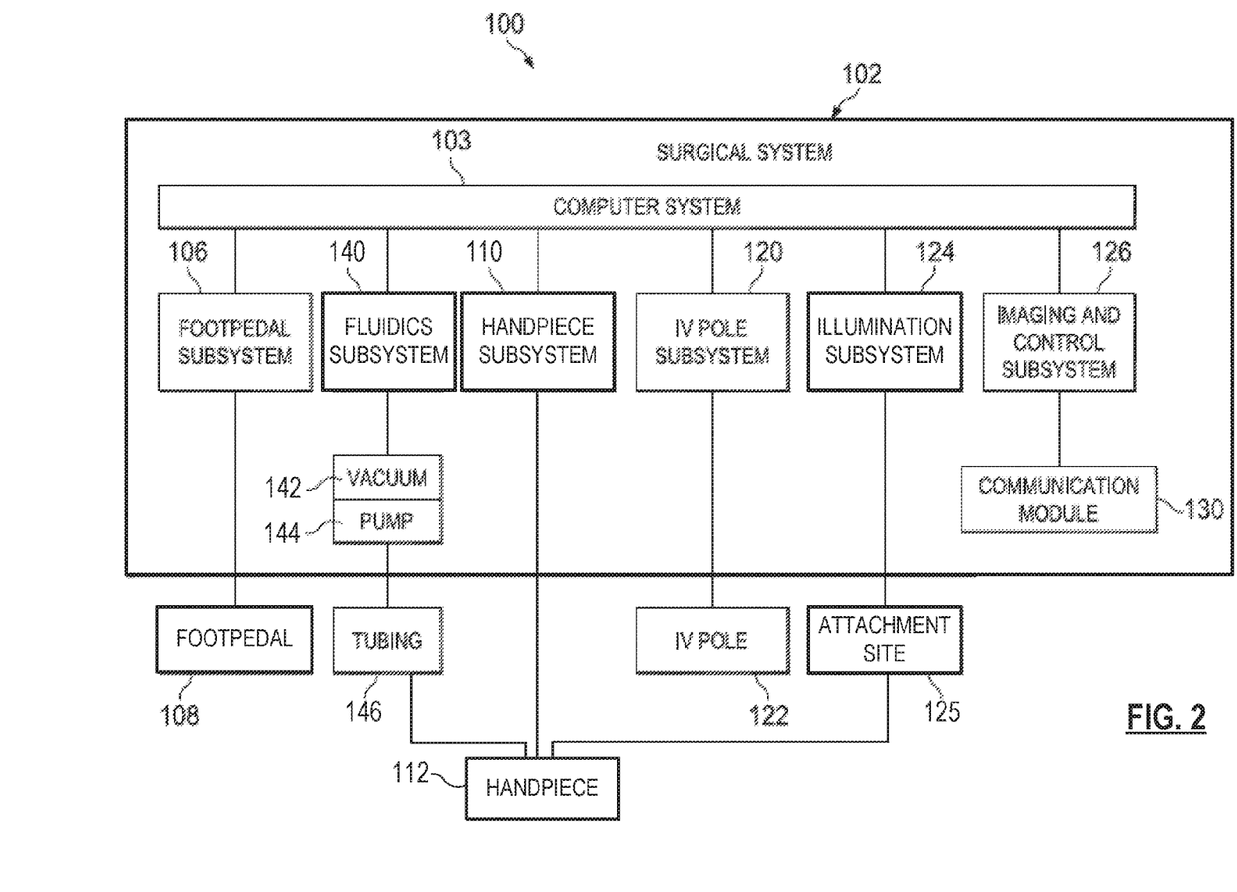
FIG. 2 is an illustration of an exemplary block diagram of the surgical system of FIG. 1, according to an aspect consistent with the principles of the present disclosure.

FIG. 2 is a block diagram of the surgical system 100 including the console 102 and several subsystems thereof. The console 102 includes a computer system 103, the display screen 104 (FIG. 1), and a number of subsystems that are used together to perform ocular surgical procedures, such as emulsification or vitrectomy surgical procedures, for example. The computer system 103 may include one or more processing devices, such as a central processing unit or central processor, and an information or data storage system. The data storage system may include one or more types of memory, such as RAM (Random Access Memory), ROM (Read Only Memory), flash memory, a disk-based hard drive, and/or a solid-state hard drive. The processing devices and storage system may communicate over a bus, which may also permit communication with and between one or more of the plurality of subsystems of the surgical system 100.

For example, the subsystems in the exemplary implementation of FIG. 2 include a footpedal subsystem 106 including, for example, a footpedal 108, a fluidics subsystem 140 including an aspiration vacuum 142 and an irrigation pump 144 that connect to tubing 146. The surgical system 100 includes a handpiece subsystem 110 including the handpiece 112, an intravenous (IV) pole subsystem 120 including a motorized IV pole 122, and an illumination subsystem 124 including an attachment site 125 whereby the handpiece 112 may couple to a light source included in the illumination subsystem 124. The illumination subsystem 124 may be referred to herein as a light source 124, although the light source may be one component of several components of the illumination subsystem 124. The surgical system 100 further includes an imaging and control subsystem 126 including a communication module 130. Other tools may be included additionally or alternatively in other embodiments. To optimize performance of the different subsystems during surgery, their operating parameters differ according to, for example, the particular procedure being performed, the different stages of the procedure, the surgeon's personal preferences, whether the procedure is being performed in the anterior or posterior portion of the patient's eye, and so on.

The different subsystems in the console 102 comprise control circuits for the operation and control of the respective microsurgical instruments or instrument components. The computer system 103 governs the interactions and relationships between the different subsystems to properly perform an ocular surgical procedure and to properly communicate information to the operator of the surgical system 100 through the display 104 and/or through a coupled microscope or wearable computing device. To do this, it includes one or more processing devices, such as a central processor, and memory and is preprogrammed with instructions for controlling the subsystems to carry out a surgical procedure, such as an emulsification procedure or a vitrectomy, for example.

In addition, the console 102 includes an input device that permits a user to make selections within a limited scope to control or modify the preprogrammed relationships between different subsystems. In this embodiment, input devices may be incorporated into the console and may include the foot-pedal 108, a touch screen device responsive to selections made directly on the screen, a standard computer keyboard, a standard pointing device, such as a mouse or trackball, buttons, knobs, or other input devices are also contemplated. Using the input devices, a surgeon, scientist, or other user may select or adjust parameters that affect the relationships between the different subsystems of the console 102. For example, a surgeon may increase or decrease an intensity of light provided by the light source 124. Additionally, a surgeon may change one or more parameters for the operation of the handpiece 112, such as an aspiration/suction parameter or an oscillation parameter of the vitreous cutting mechanism. Accordingly, based on a user input, a user may change or adjust the relationships from those that were coded into the console by the system programmers.

Because the handpiece 112 is configured to receive light from the light source 124, the surgeon may be able to visualize aspects of the surgical operations performed by or near by the handpiece 112, without requiring two incisions and without requiring the manipulation and handling of two separate devices within the small confines of the eye or in another cavity or area of the patient.

Figure 3:
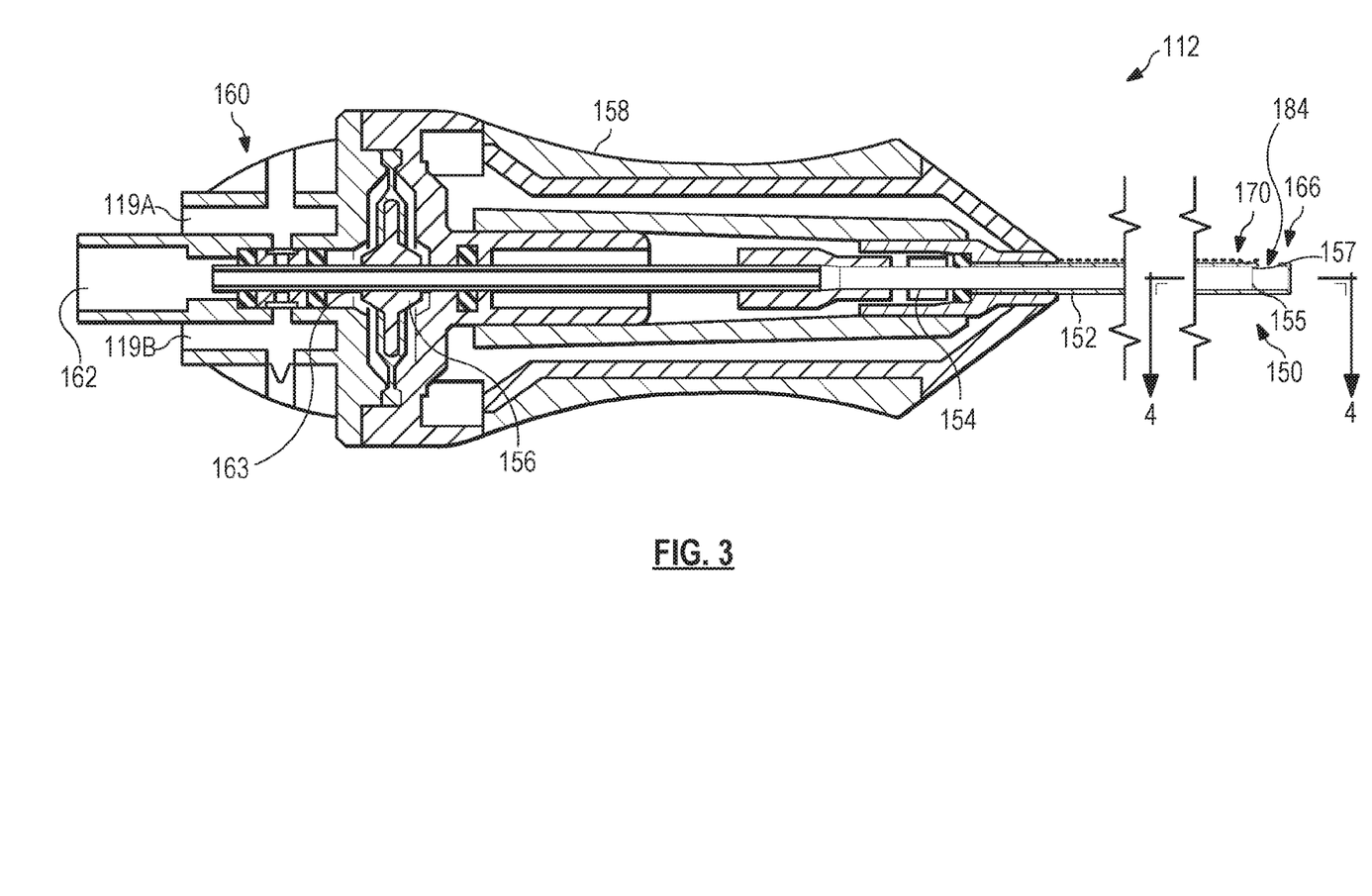
FIG. 3 is a cross-sectional illustration of an exemplary vitrectomy probe, according to aspects of the present disclosure.

FIG. 3 shows a partial cross-sectional illustration of an exemplary vitrectomy probe that may correspond with the handpiece 112 shown in FIGS. 1 and 2. In this example, the handpiece 112 may be a pneumatically-driven probe that operates by receiving pneumatic pressure alternating through first and second ports 119A and 119B. The handpiece 112 includes as its basic components a vitrectomy cutter 150 comprising an outer cutting tube 152, an inner cutting tube 154 shown in a non-cross-sectional side view, and a probe actuator or motor shown here as a reciprocating air driven diaphragm 156, all partially encased by a housing 158. The housing 158 includes an end piece 160 at the probe proximal end with the first and second air supply ports 119A and 119B and one suction port 162 to provide aspiration of liquid and tissue materials from the cutter 150.

In operation, pneumatic pressure is directed alternately from the handpiece subsystem 110 to the first and second ports 119A and 119B to operate the vitrectomy probe 112. An on-off pneumatic driver within the handpiece subsystem 110 alternates between its two positions very rapidly to alternatingly provide pneumatic pressure to the first and second ports 119A and 119B. Although shown with a single actuator or motor, other embodiments include two probe actuators or motors, one associated with each of the two ports 119A and 119B.

Figure 4:
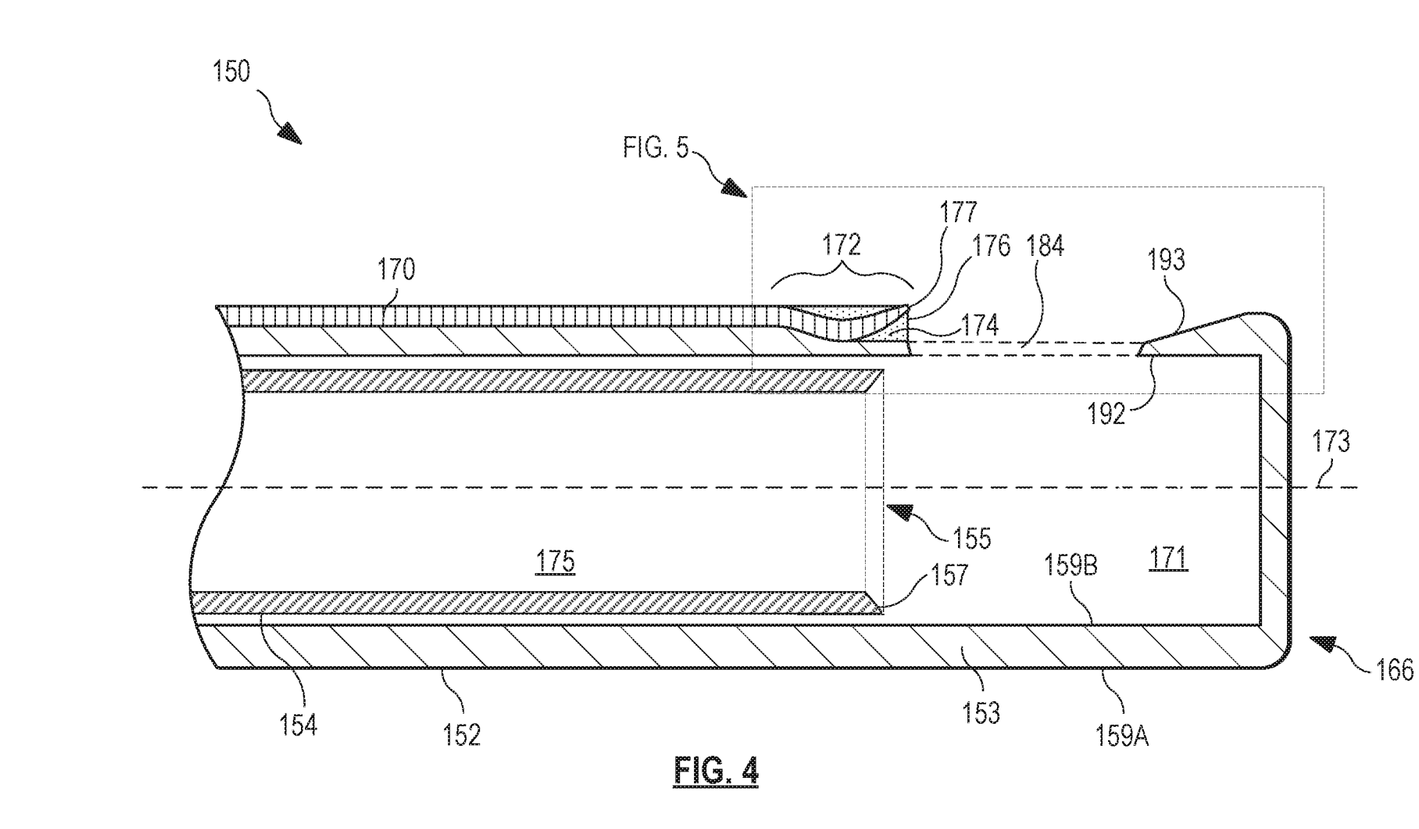
FIG. 4 is a detailed view of the distal end of the vitrectomy probe of FIG. 3, according to aspects of the present disclosure.

FIG. 3 illustrates that the cutter 150 extends from the housing 158 and includes a distal end 166, shown in FIG. 4 in greater detail. The outer cutting tube 152 and the inner cutting tube 154 may both be cylindrical tubes with a hollow bore or lumen therein. The outer cutting tube 152 has a tissue-receiving outer port 184; the inner cutting tube 154 has an open distal end 155. Generally, the inner cutting tube 154 oscillates within the outer cutting tube 152 as driven by the probe actuator. In an embodiment, the inner cutting tube 154 is driven by air pressure directed on opposing sides of the diaphragm 156. In one example of operation, if air pressure is increased at the first port 119A, the diaphragm 156 will move distally, displacing the inner cutting tube 154 relative to the outer cutting tube 152, thereby moving a first cutting edge 157 on the distal end 155 of the inner cutting tube 154 in the distal direction, past the port 184. This cuts any vitreous material which may have been aspirated into the tissue-receiving outer port 184 of the outer cutting tube 152. The vitreous may thereafter be aspirated away through the distal end 155 of the inner cutting tube 154. Venting the pressure at the first port 119A and increasing the pressure at the second port 119B moves the diaphragm 156 proximally, allowing vitreous to enter the lumen of the outer cutting tube 152 through the port 184.

In other embodiments, the probe actuator may include a piston motor in place of a diaphragm. In such embodiments, the cutter 150 is arranged so that movement of the piston also moves the inner cutting tube 154 of the cutter 150. Yet other embodiments include other types of pneumatic or electric motors that drive the inner cutting tube 154, as will be recognized by those skilled in the art.

Extending the length of the cutter 150 is an optical fiber 170, illustrated as a dashed line. Embodiments of the optical fiber 170 may be less than or equal to about 100 microns in diameter. The optical fiber 170 transmits light from the light source 124 (FIG. 2), through the attachment site 125 (FIG. 2) to the distal end 166 of the cutter 150 to illuminate the area of operation for viewing and observation by the surgeon as the surgeon removes vitreous from the eye. The optical fiber 170 may run through the housing 158, generally parallel to a shaft 163 coupling the inner cutting tube 154 to the diaphragm and then along the tubing 146 (FIG. 2) to the fluidics subsystem 140 (FIG. 2). The fluidics subsystem 140 is coupled to the handpiece 112 by the suction port 162. In other embodiments, the optical fiber 170 may extend along an outer surface of the housing 158. In yet other embodiments, the light source 124 is included within the handpiece 112 itself, such that the optical fiber 170 may not be required to extend between the handpiece 112 and the console 102.

Referring now to FIG. 4, shown therein is a detailed view of the distal end 166 of the vitrectomy cutter 150. This detailed view is cross-sectioned to more clearly illustrate certain aspects of the optical fiber 170 as included in the handpiece 112. FIG. 4 shows the distal end 166 of the vitrectomy cutter 150, including the outer cutting tube 152 and the inner cutting tube 154. As noted herein, the inner cutting tube 154 may oscillate back and forth within the lumen 171 of the outer cutting tube 152.

As shown in FIG. 4, the optical fiber 170 extends along a length of the tubular member of the outer cutting tube 152. A distal end region 172 of the optical fiber 170 is positioned within a notch 174 formed within the wall of the outer cutting tube 152. The notch 174 permits an s-curve to be formed in the distal end region 172, such that a portion of the distal end region 172 curves away from a central longitudinal axis 173 of the outer cutting tube 152 and away from the outer wall of the outer cutting tube 152. The curved distal end region 172 directs light in such a way as to improve the visibility of vitreous to the operating surgeon. While the more proximal portion of the distal end region 172 is supported by the outer cutting tube 152, as shown in FIG. 4, the more distal portion of the distal end region 172 is surrounded by an opaque adhesive material 176 that adheres the distal end region 172 to the notch 174 and generally fills the portions of the notch 174 not occupied by the distal end region 172.

The distal end region 172 is positioned proximate the tissue-receiving port 184, which may be an opening through the tubular wall 153 of the outer cutting tube 152. The port 184 may have a diameter ranging from about 5 mm to about 1 mm. The tubular wall 153 includes an outer surface 159A and an inner surface 159B. The port 184 extends through the wall 153 to permit vitreous to enter into the lumen 171 of the outer cutting tube 152 for cutting and aspiration by the cutting edge 157 at the open distal end 155 of the inner cutting tube 154. The vitreous is then aspirated through an inner lumen 175 of the inner cutting tube 154 and out of the eye. While this process is repeatedly performed to remove the vitreous or a portion thereof, light is emitted from a tapered distal tip portion 177 of the optical fiber 170 at the most distal portion of the distal end region 172. The light illuminates the vitreous in the area around the port 184 so that the surgeon can tell when it has been removed and can position the distal end of the cutter 150 to remove more if desired.

Figure 5:
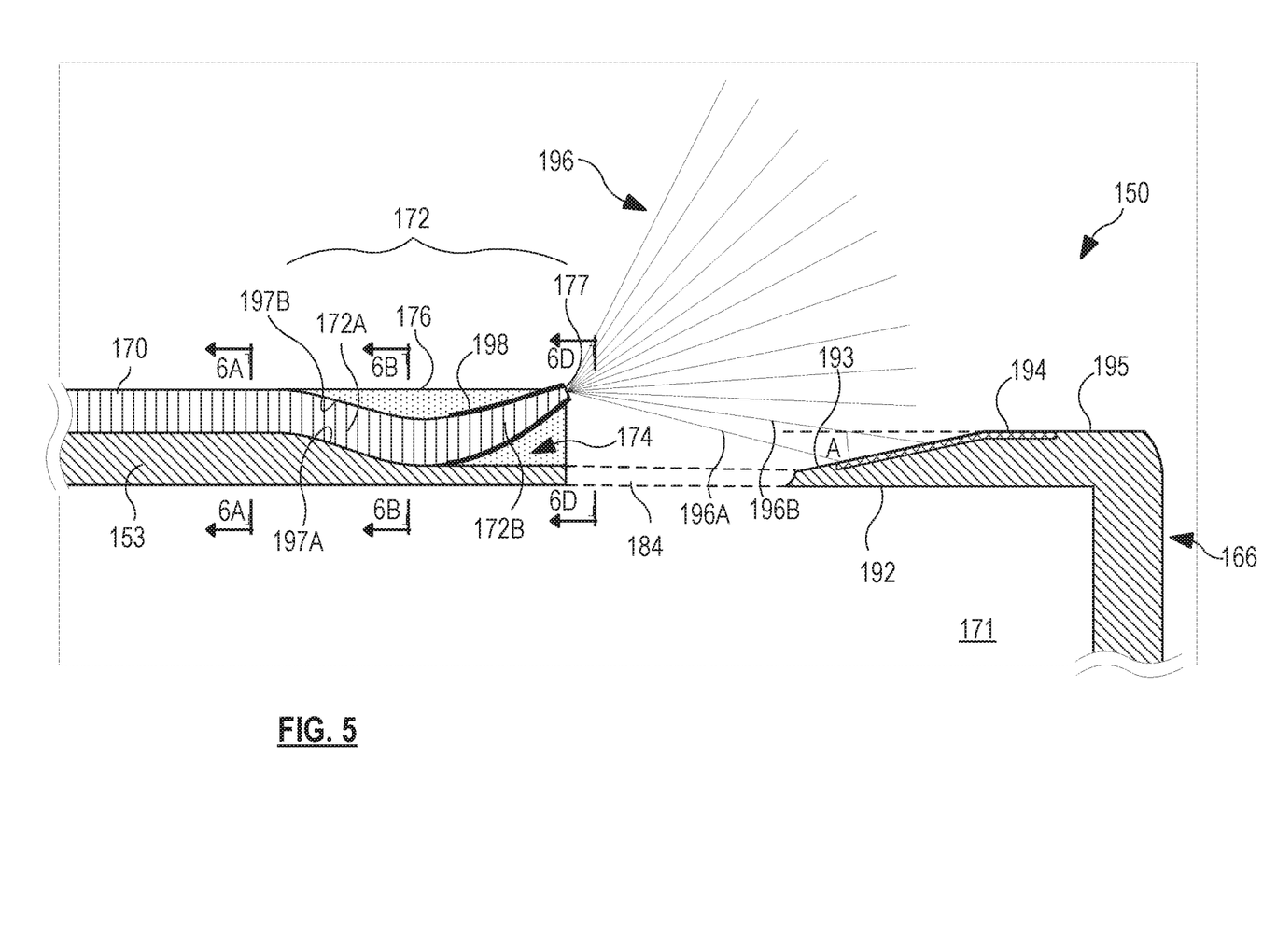
FIG. 5 is a detailed view of a portion of the distal end of the vitrectomy probe included in a dashed line box in FIG. 4, according to aspects of the present disclosure.

FIG. 5 shows a detailed view of a portion of the cutter 150 identified by the dashed line box shown in FIG. 4. It illustrates further details of the optical fiber 170. As illustrated in FIG. 5, the distal end 166 of the outer cutting tube 152 includes a cutting portion 192 proximate to the port 184 and on a distal side thereof. This portion 192 extends towards the port 184 and comprises a tapered or angled section of the wall 153 of the outer cutting tube 152 that provides a sharper surface with which to cut the vitreous.

The cutting portion 192 comprises an angled section 193 on the outer surface 159A of the wall 153 of the outer cutting tube 152. The angled section 193 and a portion of a parallel section 195 (the parallel surface being defined as parallel to the central longitudinal axis 173 of the outer cutting tube 152) include a treated surface 194. The treated surface 194 is an anti-glare surface that minimizes certain problems that may arise due to reflection of emitted light 196, which is emitted from the optical fiber 170. Multiple rays of the emitted light 196 are illustrated to show the general direction of light emitted from the optical fiber 170 into the vitreous. The treated surface 194 may include a portion on the angled section 193 and a portion on the parallel section 195, in some embodiments. Other embodiments may include a portion of the treated surface 194 included only on the angled section 193. Yet other embodiments may include a treatment to all exposed surfaced adjacent to the port 184, such that all the exposed surfaces adjacent to the port 184 are treated surfaces.

For example, the light represented by the rays 196A and 196B may be incident on the treated surface 194. In order to prevent glare or non-uniform illumination caused by interactions with the angled section 193 of the cutting portion 192, the treated surface 194 may be an absorptive surface that absorbs the light represented by the rays 196A and 196B. For example, the absorptive surface of the treated surface 194 may be a roughened surface provided by mechanically or chemically roughening the angled section 193 of the cutting portion 192. In other embodiments, the treated surface 194 may be a specular surface that redirects light at a specific angle determined by the angle of incidence on the treated surface 194. The treated surface 194 may be chemically and/or mechanically polished in order to provide the specular surface. The angle A of the angled section 193 of the cutting portion 192 may also reduce glare produced by the interaction of the light 196 and the outer surface of the outer cutting tube 152. Angle A may range from about 3 degrees to about 30 degrees.

As illustrated in FIG. 5, the distal end region 172 of the optical fiber 170 includes a first portion 172A (a less distal portion of the distal end region 172 that curves into the notch 174 toward the central axis 173 of the outer cutting tube 152) and a second portion 172B (a more distal portion of the distal end region 172 that curves away from or out of the notch 174, away from the central axis 173 of the outer cutting tube 152). Embodiments of the distal end region 172 may have a length ranging from about 15 mm to less than 5 mm. The distal end region 172 may have a length of about 3 or 4 mm in some shorter embodiments. The curve of the first portion 172A permits the curve of the second portion 172B to curve away from the outer cutting tube 152 without protruding substantially beyond a general diameter of the outer cutting tube 152. The curve of the second portion 172B directs light away from the outer cutting tube 152. By directing the light 196 away from the outer cutting tube 152, the illustrated optical fiber 170 may produce less glare and may produce more uniform illumination within the eye. While the illustrated embodiment in FIG. 5 shows the rays 196A and 196B as being directed to and as contacting the treated surface 194, in other embodiments, none of the light 196 emitted from the optical fiber 170 is incident upon the angled section 193 of the outer cutting tube 152.

As illustrated, a bottom side 197A of the first portion 172A is in contact with the outer surface 159A of the wall 153 of the outer cutting tube 152. The first portion 172A may be located in a notch 174 formed in the wall 153. While not explicitly illustrated, the first portion 172A may be affixed to the outer cutting tube 152 (within the notch 174) by an adhesive. The top side 197B of the first portion 172A may be in contact with the opaque adhesive 176. The opaque adhesive 176 may be an epoxy or another material that can be applied in a soft or softened state, but which hardens thereafter. The opaque adhesive 176 generally surrounds the second portion 172B and supports it as it curves away from the central axis 173 and the outer surface 159A of the outer cutting tube 152. The second portion 172B is also surrounded with a coating 198 that further prevents light from escaping out of the optical fiber 170. The coating 198 may be a metallized coating, such as a foil coating. In some embodiments, the coating 198 is provided by a capping structure that is formed separately from the taper of the second portion 172B and is affixed thereto thereafter. The capping structure may be used to provide the tapered shape of the second portion 172B. While light is prevented from escaping at the sides of the distal end region 172, a tip of the second portion 172B allows emission of light 196 from the distal tip portion 177. The tip portion 177 of the second portion 172B may be positioned adjacent to or proximate to the port 184 as shown in order to maximize irradiance at the port 184.

Figure 6A:
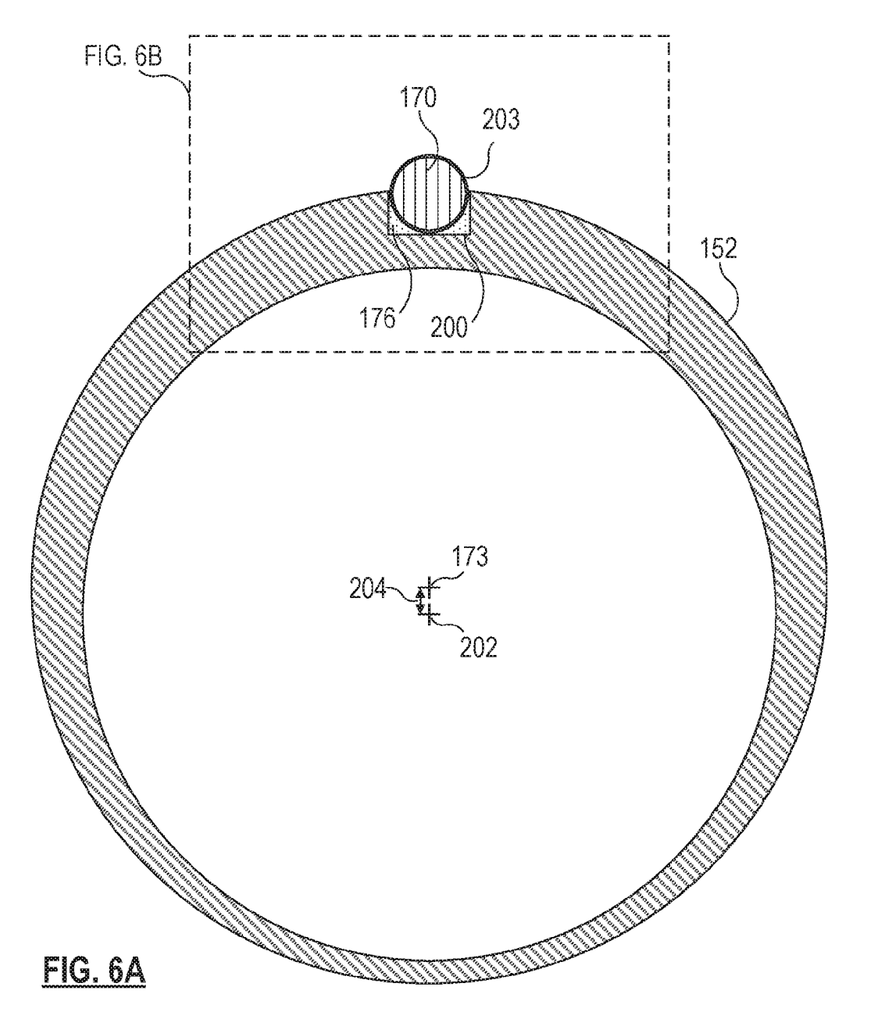
FIGS. 6A, 6B, 6C, and 6D are cross-sectional views of the vitrectomy probe obtained along respective lines in FIG. 5, according to aspects of the present disclosure.
Figure 6B:
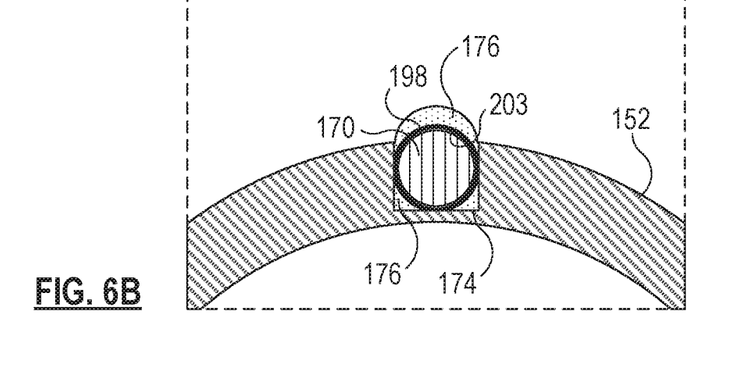
Figure 6C:
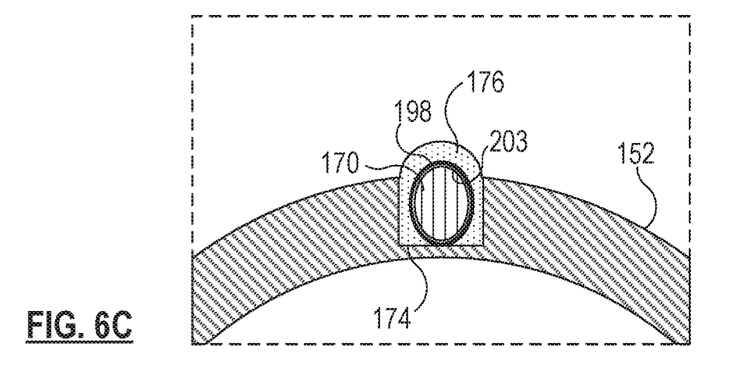

FIGS. 6A, 6B, 6C, and 6D show cross-sections of the cutter 150 taken respectively along the lines 6A, 6B, and 6D of FIG. 5. FIG. 6C shows an alternative implementation.

FIG. 6A illustrates a complete cross-section of the outer cutting tube 152. In the implementation shown, the outer cutting tube 152 includes a grooved portion or a groove 200 formed in the outer surface 159A of the wall 153. In some embodiments, the grooved portion or groove 200 comprises a flat on the outer surface 159A rather than a deeper groove extending into the wall 153 of the outer cutting tube 152. In some examples, the grooved portion or groove 200 extends longitudinally along the entire length of the outer cutting tube 152 or along a substantial portion of the outer cutting tube 152. The groove 200 may be formed by various methods, such as deep drawing, laser cutting, a cutting wheel, milling, chemical etching, electrical discharge machining. The outer cutting tube 152 may be formed with a larger outer diameter to facilitate the formation of the groove 200. After the groove 200 is formed, the outer cutting tube 152 may then be ground down to provide the final outer dimension.

The groove 200 permits at least a portion of the diameter of the optical fiber 170 to be positioned within an outer diameter of the outer cutting tube 152. In the example shown, about half the diameter of the optical fiber 170 is positioned within the groove 200. As illustrated, the groove 200 includes squared corners; however, some embodiments may include a different profile. For example, the groove 200 may have a circular or elliptical cross-section or a generally rectangular cross-section having rounded corners. As illustrated, the opaque adhesive 176 is included in the groove 200 in order to affix the optical fiber 170 along a length of the outer cutting tube 152. The optical fiber 170 may be secured within the longitudinal groove 200 by applying an adhesive material, such as the opaque adhesive 176, therein. Alternatively, the optical fiber 170 may be soldered to the outer cutting tube 152, in some embodiments. In other embodiments, a heat shrinking sleeve may be placed around the outer cutting tube 152 and the optical fiber 170 and shrunk to secure these components together. In some embodiments, the optical fiber 170 may include a coating, such as a thermoplastic adhesive that can be used to bond the components together when subjected to activating thermal energy. In some embodiments, a coating may be applied over the optical fiber 170 and the outer cutting tube 152 to seal them together.

In the implementation illustrated in FIG. 6A, the optical fiber 170 may include a fiber cladding 203 that surrounds and protects the optical fiber 170. The cladding 203 may be an opaque outer coating that also prevents the escape of light from the optical fiber 170. The cladding 203 may be a thinner layer of the same material that provides the coating 198, in some embodiments. In other embodiments, the cladding 203 and the coating 198 may be formed of different materials and the coating 198 may be thinner than the cladding 203. For example, the cladding 203 may be an opaque polymer material, while the coating 198 is a metal layer.

Figure 6D:
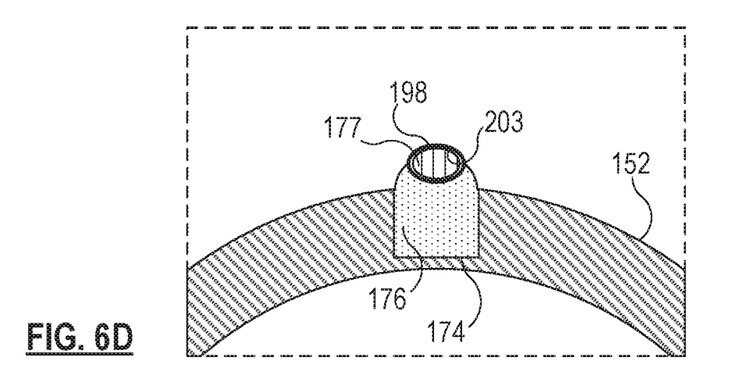

FIG. 6A further illustrates two central axes associated with the outer cutting tube 152. The outer cutting tube 152 comprises the outer surface 159A and the inner surface 159B of the wall 153. While the outer surface 159A is associated with the central axis 173, the inner surface 159B of the wall 153 of the outer cutting tube 152 is associated with an offset inner surface axis 202 at the center of the lumen 171 defined by the inner surface 202. The offset 204 between the central axis 173 and the inner surface axis 202 may be in a range from about 0.001 mm to about 0.025 mm. The offset 204 between the axes 173 and 202 provides a greater thickness for the wall 153 on the side of the outer cutting tube 152 occupied by the optical fiber 170 and a thinner portion of the wall 153 on the opposite side. This permits more of the material of the wall 153 to be present near the optical fiber 170, which may provide for a deeper groove 200 and a deeper notch 174 (FIGS. 6B-D). The deeper groove 200 may permit the overall gauge of the outer cutting tube 152 to remain effectively equivalent to a desired gauge size or smaller. For example, the outer cutting tube 152 may be a 23 gauge needle. While the protruding portion of the optical fiber 170 may technically violate a desired gauge size (e.g., 23 gauge), the violation may be small enough to permit the cutter 150 to be inserted through a desired port size or trocar size, conforming to the desired gauge size, as it is inserted into the eye of a patient. In some embodiments, the offset 204 is present along the entire length of the outer cutting tube 152. In other embodiments, the offset 204 may be present only in a distal portion of the outer cutting tube 152.

For simplicity of understanding, FIGS. 6B, 6C, and 6D show a cross-section of only a portion of the cutter 150 including the optical fiber 170. As such, FIG. 6B shows only a portion of a cross-section along the line 6B-6B of FIG. 5. FIG. 6B shows that, when the optical fiber 170 is at the bottom of the notch 174, a portion of the opaque adhesive 176 may overlay the optical fiber 170 and its cladding 203. A portion of the coating 198 is shown in FIG. 6B as being deposited or formed over the cladding 203. In some embodiments, the coating 198 may overlay only a portion of the cladding 203. In other embodiments, the coating 198 may begin where the cladding 203 ends, such that the full length of coating 198 is formed directly in contact with the optical fiber 170.

FIG. 6C illustrates an alternative embodiment of a portion of the cross-section indicated by the line 6B-6B of FIG. 5. As shown in FIG. 6C, the optical fiber 170 and the surrounding coating 198 have a non-circular shape. The depicted embodiment of the optical fiber 170 has an oval or an elliptical cross-section, rather than a circular cross-section. In some embodiments, the major of the ellipse or oval is oriented along a radius of the outer cutting tube 152. In other embodiments, the major of the ellipse or oval may be oriented along a circumference around the axis 173 of the outer cutting tube 152. This shape of the optical fiber 170 may enable the entire optical fiber 170 to be positioned within the notch 174 in the outer surface 159A of the wall 153 and may provide for the concentration of light in the distal portion 172B prior to emission from the distal tip of the optical fiber 170. As is apparent from the cross-sections of FIG. 6A in comparison with FIGS. 6B and 6C, the notch 174 extends further into the wall 153 of the outer cutting tube 152 toward the inner surface 159B than the groove 200 does. For example, the groove 200 may range from about 0.001 mm to about 0.025 mm in depth, while the notch 174 may range from about 0.001 mm to about 0.05 mm in depth.

FIG. 6D is a cross-section as seen along the line 6D-6D of FIG. 5, the distal tip 177 of the optical fiber 170 appears elliptical or oval due to its angling away from the axis 173 (FIG. 6A) of the outer cutting tube 152 and away from a central axis of the optical fiber 170 itself. The supporting opaque adhesive material 176 maintains the distal tip 177 in the illustrated off-axis pose to direct light emitted from the distal tip 177 in a direction away from the cutting portion 192 of the outer cutting tube 152 on the side opposite the port 184. The distal tip 177 of the optical fiber 170 is positioned proximate the port 184 to provide the maximum amount of light into the vitreous at the port 184 of the cutter 150.

Figure 7A:
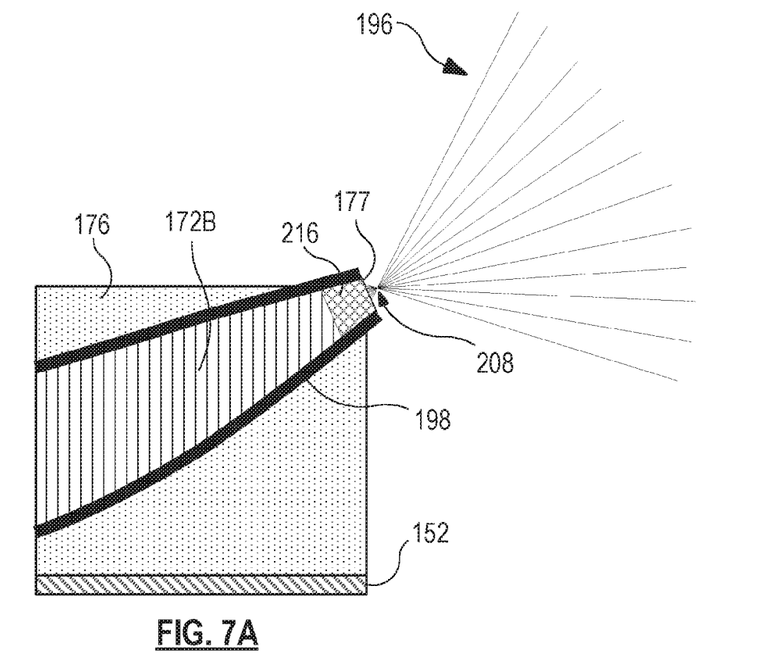
FIGS. 7A, 7B and 7C present cross-sectional views of alternative embodiments of a distal tip of an optical fiber included in the vitrectomy probe of FIG. 4, according to aspects of the present disclosure.
Figure 7B:
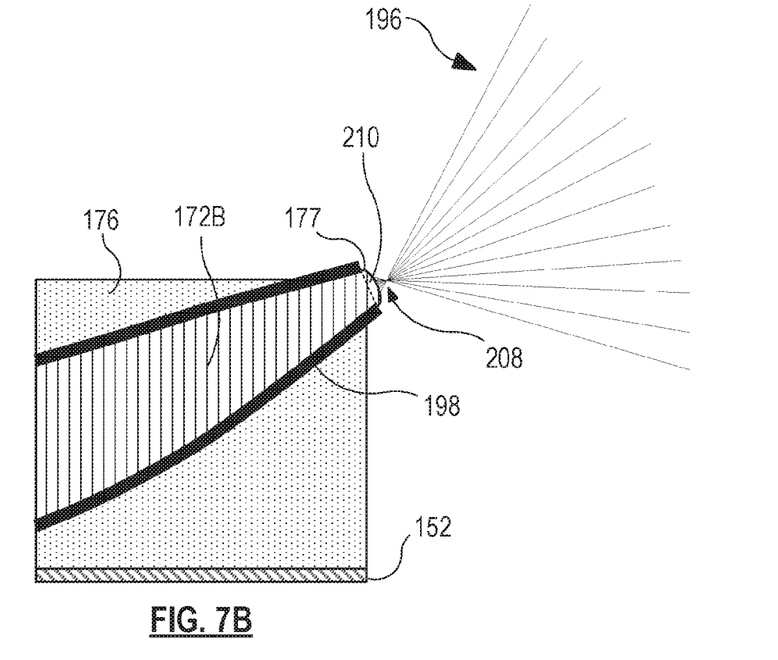
Figure 7C:
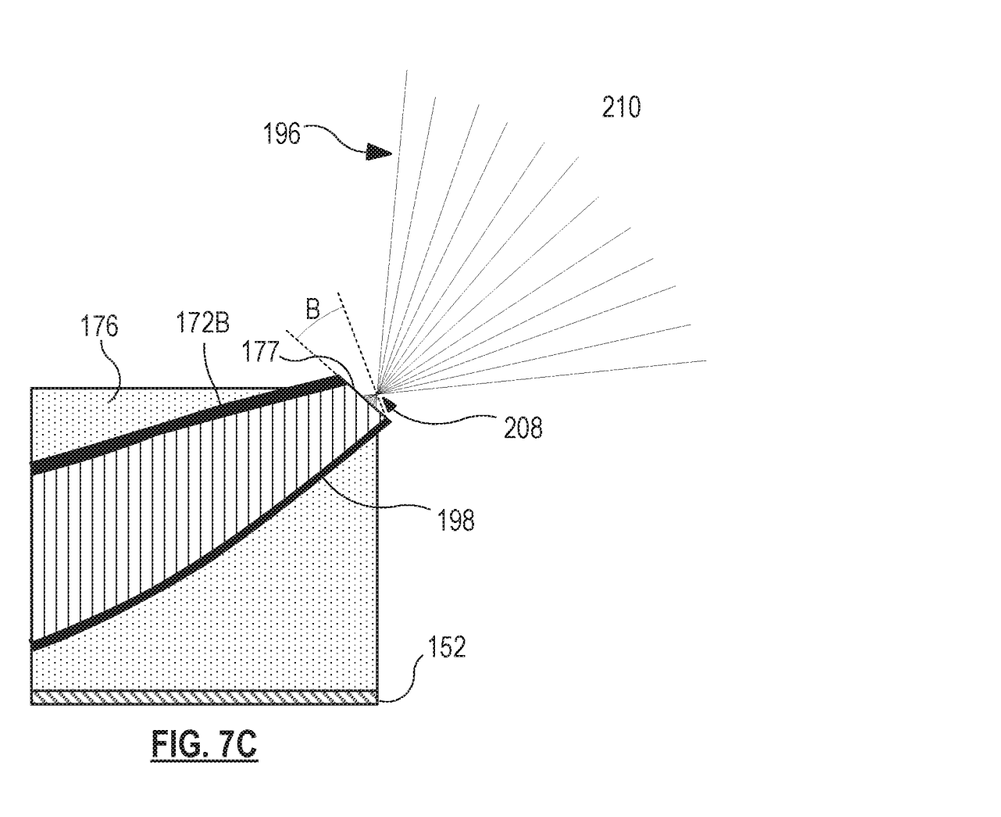

Referring now to FIGS. 7A, 7B, and 7C, shown therein are cross-sectional views of a distal region of the second portion 172B of the distal end region 172 of the optical fiber 170. FIGS. 7A-C illustrate embodiments of the distal tip 177. In the embodiment illustrated in FIG. 7A, the distal tip 177 includes a gradient-index lens or GRIN lens 216, provided by a gradient in the index of refraction of the optical fiber at the distal tip 177. The GRIN lens 216 provided at the distal tip 177 focuses the emitted light at a focal point 208. The focal point 208 may be selected by controlling the gradient at the distal tip 177. The focal point 208 may be such that the light is focused and concentrated in the near field while diffuse in the far field of the beam, relative to the distal tip 177. The views illustrated in FIGS. 7A and 7B are not necessarily drawn to scale, particularly with respect to the focal point 208, which may be a millimeter or more away from the distal tip 177, in some embodiments.

Similarly, FIG. 7B illustrates an optical lens 210, such as a ball lens, positioned at the distal tip 177 to focus the emitted light to provide maximum illumination proximate the port 184. The optical lens 210 may comprise additional optical fiber material at the distal tip 177 or may be a pre-formed lens affixed to the distal tip 177 during fabrication of the optical fiber 170, and particular of the distal end region 172 thereof. The optical lens 210 provides a focal point 208 that can be moved closer to or further away from the distal tip 177 in order to maximize illumination in the vitreous in front of the port 184 to better enable the surgeon to visualize and remove the vitreous.

FIG. 7C illustrates an embodiment of the distal tip 177 that includes a beveled end. The beveled end is formed at a bevel angle B to allow light escaping the fiber end to refract away from the outer cutting tube 152. While the distal tip 177, as shown in FIGS. 7A and 7B, may be substantially orthogonal to a central axis extending within the distal end region 172, the beveled end of the distal tip 177, as shown in FIG. 7C, may be off-orthogonal by several degrees. For example, the bevel angle B may range from about 2 to about 15 degrees. In other embodiments, the bevel angle B may range from about 15 degrees to about 45 degrees. The beveled end of the distal tip 177 may be beveled away from the outer cutting tube 152 so as to direct the emitted light 196 away from the outer cutting tube 152, particularly away from the outer surface of the protruding cutting portion 192 in order to decrease the amount of light reflected therefrom. In other embodiments, the bevel angle B may be angled toward the outer cutting tube 152. In such embodiments, the curve of the second distal portion 172B may direct emitted light 196 away from the outer cutting tube 152 more than the bevel angle B directs light 196 toward the outer cutting tube 152. In some embodiments, the distal tip 177 including the beveled end may not be curved away from the outer cutting tube 152 (and instead, may rely on the beveled end to refract the light away from the outer cutting tube 152).

While FIGS. 7A, 7B, and 7C illustrate a focal point 208 that is positioned a distance away from the distal tip 177, other embodiments may not focus the emitted light in this manner. Other embodiments may cause the controlled dispersion of light from the distal tip, without focusing the light at any point.

Embodiments of the present disclosure may include methods of performing a surgical procedure using an illuminated surgical device, like the vitrectomy cutter 150 described herein. In an ophthalmic example, a surgeon may make an incision in the eye of a patient. The surgeon may then insert the vitrectomy cutter 150 through the incision. In some embodiments, a trocar cannula may be positioned in the incision and the cutter 150 may be advanced therethrough. The surgeon may then power the illumination subsystem by powering the light source, and illuminate the vitreous around the port 184 of the cutter 150 while removing the vitreous. The illumination may enable to surgeon to better see the vitreous in order to remove it more effectively and safely. After the desired portion of the vitreous is removed, the cutter 150 may be removed from the eye.

Through use of principles described herein, a user can have a better experience when viewing the surgical site. Specifically, the user may be better able to visualize the clear vitreous by illuminating the vitreous and vitreous fibers therein in an area proximate to the port of the vitreous cutter. The focal point of the illumination or the area of the illumination may be controlled to limit or prevent glare from resulting due to interactions between the light and the distal end of the outer cutting tube of the vitreous cutter. The focal point may also limit or prevent the appearance of a bright spot on the retina that may reflect sufficient light to make visualizing the vitreous more difficult.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An illuminated microsurgical instrument comprising:
    a microsurgical instrument having a tubular member arranged to treat patient tissue at a surgical site, the tubular member having a distal tip and an outer surface; and
    an optical fiber arranged to deliver light to the surgical site, the optical fiber including a proximal end arranged to receive a light beam from a light source and also including a distal end with a fiber distal tip that includes a beveled end arranged to refract light away from the tubular member outer surface;
    wherein the outer surface of the tubular member has a notch formed therein;
    wherein the outer surface includes a longitudinal groove formed therein, the optical fiber extending along the tubular member within the longitudinal groove, the notch having a depth greater than a depth of the longitudinal groove;
    wherein the optical fiber is seated in the notch.

2. The illuminated microsurgical instrument of claim 1, wherein the optical fiber is attached to the tubular member through an adhesive.

3. The illuminated microsurgical instrument of claim 1, wherein the fiber distal tip is not curved away from the tubular member.

4. The illuminated microsurgical instrument of claim 1, wherein the fiber distal tip is curved away from the tubular member.

5. The illuminated microsurgical instrument of claim 1, further comprising a sleeve around the tubular member and the optical fiber.

6. An illuminated microsurgical instrument comprising:
a microsurgical instrument having a tubular member arranged to treat patient tissue at a surgical site, the tubular member having a distal tip and an outer surface; and
an optical fiber arranged to deliver light to the surgical site, the optical fiber including a proximal end arranged to receive a light beam from a light source and also including a distal end with a fiber distal tip that includes a beveled end arranged to refract light away from the tubular member outer surface;
wherein the outer surface of the tubular member has a notch formed therein;
wherein the outer surface includes a longitudinal groove formed therein, the optical fiber extending along the tubular member within the longitudinal groove, the notch having a depth greater than a depth of the longitudinal groove;
wherein the distal end of the optical fiber is a curved distal end arranged to emit light adjacent to the distal tip, a portion of the curved distal end being positioned within the notch, the curved distal end curving away from the tubular member.

7. The illuminated microsurgical instrument of claim 6, wherein the curved distal end of the optical fiber comprises a tapered fiber tip portion, wherein the tapered fiber tip portion of the curved distal end of the optical fiber comprises an opaque coating thereon.

8. The illuminated microsurgical instrument of claim 6, wherein the curved distal end of the optical fiber comprises:
a first portion that curves into the notch; and
a second portion that curves out of the notch.

9. The illuminated microsurgical instrument of claim 6, wherein the curved distal end is affixed within the notch by an opaque adhesive material that surrounds a portion of the curved distal end.

10. The illuminated microsurgical instrument of claim 6, wherein a central axis of a lumen extending within the tubular member is offset from a central axis of the outer surface of the tubular member such that a thickness of the tubular member is greater on a side comprising the optical fiber than a thickness of the tubular member on an opposite side.

11. The illuminated microsurgical instrument of claim 6, wherein the tip of the curved distal end comprises a lens that focuses the light beam in a near field of the light beam and diverges the light beam in a far field of the light beam.

12. The illuminated microsurgical instrument of claim 6, wherein the microsurgical instrument is a vitrectomy probe.

13. The illuminated microsurgical instrument of claim 6, wherein the outer surface of the tubular member comprises an angled section that provides a cutting edge disposed distal of a port on the tubular member outer surface, wherein at least the angled section comprises an anti-glare surface.

14. A surgical system, the surgical system comprising:
a light source coupleable to an optical fiber to provide illumination at a distal end of the optical fiber; and
a vitrectomy subsystem having a vitrectomy cutter, the vitrectomy cutter including:
a tubular member with a distal tip and a lumen extending therein, the lumen being defined by an inner surface of a wall of the tubular member, the distal tip including a port extending through the wall of the tubular member; and
the optical fiber arranged to deliver light to a surgical site, the optical fiber including a proximal end for receiving a light beam from the light source and a distal end arranged to emit light adjacent to the port, a portion of the distal end being positioned within a notch extending from an outer surface of the tubular member into the wall, wherein a tip of the distal end is directed away from the tubular member;
wherein the outer surface includes a longitudinal groove formed in the wall, the optical fiber extending along the tubular member within the longitudinal groove, wherein the notch has a depth greater than a depth of the longitudinal groove.

15. The surgical system of claim 14, wherein the distal end of the optical fiber comprises:
a less distal portion that curves into the notch; and
a more distal portion that curves away from the lumen.

16. The surgical system of claim 14, wherein the distal end is affixed within the notch by an opaque adhesive material that surrounds a portion of the distal end.

17. The surgical system of claim 14, further comprising a sleeve around the tubular member and the optical fiber.

18. A vitrectomy cutter comprising:
a tubular member arranged to remove vitreous from within an eye of a patient, the tubular member having a distal tip and a lumen extending therein, the lumen being defined by an inner surface of a wall of the tubular member, the distal tip comprising a port extending through the wall of the tubular member to receive vitreous into the lumen; and
an optical fiber arranged to deliver light into the eye, the optical fiber including a proximal end to receive a light beam from a light source and also including a distal end arranged to emit light adjacent to the port, a portion of the distal end being positioned within a notch formed in an outer surface of the tubular member, a portion of the distal end directed away from the tubular member;
wherein the outer surface of the tubular member includes a longitudinal groove formed therein, the optical fiber extending along the tubular member within the longitudinal groove, the notch having a depth greater than a depth of the longitudinal groove.

19. The vitrectomy cutter of claim 18, wherein the distal end of the optical fiber comprises:
a first portion that curves into the notch; and
a second portion that curves out of the notch, the second portion being tapered, wherein a cross-sectional shape of at least part of the second portion of the distal end is oval.

20. The vitrectomy cutter of claim 18, wherein a distal side of the port comprises an angled section that provides a cutting edge and wherein the angled section is treated to be one of a specular surface or an absorptive surface.

21. The vitrectomy cutter of claim 18, wherein a tip of the distal end of the optical fiber comprises a ball lens or a gradient-index (GRIN) lens that focuses the light beam in a near field of the light beam and diverges the light beam in a far field of the light beam.

* * * * *